United States Patent [19]

Schultz

[11] Patent Number: 4,932,977

[45] Date of Patent: Jun. 12, 1990

[54] INDOLE-ALDEHYDE HAIR DYES

[75] Inventor: Thomas M. Schultz, Highland Mills, N.Y.

[73] Assignee: Clairol Incorporated, New York, N.Y.

[21] Appl. No.: 274,110

[22] Filed: Nov. 21, 1988

[51] Int. Cl.$^5$ .................... A61K 7/13; A61K 7/42; A61K 7/44; C09B 67/00

[52] U.S. Cl. .................................. 8/423; 8/429; 8/608; 8/408; 8/407; 8/406

[58] Field of Search ............... 8/423, 406, 407, 608, 8/408, 429; 512/1, 2

[56] References Cited

U.S. PATENT DOCUMENTS

| | | |
|---|---|---|
| 852,943 | 5/1907 | Fortner .................................. 8/608 |
| 3,194,734 | 7/1965 | Seemuller et al. |
| 4,620,850 | 11/1986 | Bachmann et al. .................. 8/423 |
| 4,695,285 | 9/1987 | Chung-Bong-Chan et al. ....... 8/407 |
| 4,776,857 | 10/1988 | Carrol et al. ........................ 8/423 |
| 4,808,190 | 2/1989 | Grollier et al. ...................... 8/423 |
| 4,808,569 | 2/1989 | Chaudhuri et al. .................. 512/2 |

Primary Examiner—A. Lionel Clingeman
Assistant Examiner—J. E. Darland
Attorney, Agent, or Firm—S. M. Nolan

[57] ABSTRACT

Combined indole-aldehyde compositions for dyeing natural fibers, particularly for coloring human hair, are taught wherein the combined indole-aldehyde composition is either preformed or reacted in site on the natural fiber under acidic conditions. A method employing said compositions is also taught.

16 Claims, No Drawings

INDOLE-ALDEHYDE HAIR DYES

FIELD OF THE INVENTION

This invention relates to dyeing compositions particularly suitable for coloring human hair. The dyeing compositions employ a combined indole-aldehyde composition as the coloring agent, which is either preformed or reacted in situ on the hair.

BACKGROUND OF THE INVENTION

Coloring of hair with a permanent or long wearing dye generally involves the oxidative reaction of a phenylenediamine, typically in the presence of a hydroxybenzene derivative to produce the indo-dye. An aryldiamine is normally mixed with a solution consisting of an oxidizing agent, usually hydrogen peroxide, and another agent such as a resorcinol. This mixture is then applied to the hair for a period of time long enough to impart a color which is resistant to shampooing and being rubbed off. With such a permanent dyeing system the color is formed within the hair fiber and is therefore trapped and not able to diffuse out. Permanent hair coloring procedures are usually performed at an alkaline pH between pH 8.5 and 11, which can cause some damage to the hair. Such oxidative dyeing of hair is generally accompanied by the readily perceptible deterioration of tactile properties of hair manifesting themselves in a raspy feel and increased difficulty in combing.

The alkaline conditions under which the treatment procedure must be carried out further damages the hair and effects the morphological changes in the cuticular surface of the hair fibers as described by Mahrle, et al., "The Use of SEM to Assess Damage to Hair" in *Hair Research*; edited by C. E. Orfauos, W. Montagna and G. Stittgen; (Springer-Verlag; New York, 1981).

Although practically speaking most, if not all, permanent hair coloring procedures are performed with alkaline media, neutral to acidic permanent hair coloring processes have been taught. For example, Shesiedo (JP 53130443) teaches that the combination of a trihydroxybenzene with a metal salt of Cu(II), Fe(II) or Mn(II) in contact with hair over 60 minutes at pH 7 will impart a dark color to the hair. Very gradual hair coloring at pH less than 6 is taught in JP 85039645 (Bristol-Myers) by using a trihydroxybenzene or a trihydroxytoluene and a phenylenediamine in combination with air as the oxidant. Brown shades are achieved after repeated applications of the mixture.

It is nonetheless apparent from the prior art that alkaline solutions of oxidizing materials are required in order to permanently dye hair in a relatively short period of time to achieve colors other than black or brown.

Typical of various prior art references related to the field of this invention are the following:

U.S. Pat. No. 4,620,850 (Bachmann et al.) discloses a composition for dying hair comprising derivatives of indole. The composition further comprises compounds such as protocatechualdehyde. The dyeing takes place at pH 2 to 4;

U.S. Pat. No. 3,871,818 (Kinney et al.) which discloses a solution containing an alkyl dialdehyde compound in combination with at least one nitrogen containing compound for changing the color of keratinous materials, particularly human nails;

U.S. Pat. No. 4,695,285 (Chung-Bong-Chan et al.) which discloses the use of azidoindole for dyeing hair. The composition may also comprise a color coupler for interacting with azidoindole;

U.S. Pat. No. 4,453,941 (Jacobs) which discloses a hair dye composition comprising indole derivatives in admixture with certain compounds having a reactive nitrogen moiety;

U.S. Pat. No. 4,391,603 (Rosenbaum et al.) which discloses the use of hydroxyl derivatives of benzaldehyde for coloring keratin fibers without an oxidizing agent.

None of the foregoing references nor any other prior art teaching of which the applicant is aware discloses the use of the method and compositions disclosed in the present application.

SUMMARY OF INVENTION

The present invention is directed to dyeing compositions and a method of using same, particularly for dyeing hair and other natural fibers employing as the coloring agent a combined indole-aldehyde reaction product which is either preformed or reacted in situ on the hair.

DESCRIPTION OF THE INVENTION

It has been found that employing a combination of an indole with an aldehyde at unadjusted pH and applying this combination to the hair, will result in a permanent hair color. It has also been discovered that the described reaction proceeds quickly and that the dyed hair has no rub-off of the dye after shampooing. It has, therefore, been concluded that the color forming process is occurring within the fibers of the hair.

In making the determination and observations upon which the present invention is based, it was determined that the reaction between 4-N,N-dimethylamino-benzaldehyde and pyrrolic compounds provides a simple colorimetric assay for the latter materials. In order to carry out such an assay, the aldehyde is dissolved in 50% water-ethanol at pH 3, this solution is known as Ehrlich's reagent and has been used for the detection of pyrroles and indoles since 1901. It has further been found that upon extending the use to other aldehydes with a variety of indoles, the reaction is quite general. Rapid color formation occurs, with the specific combination of a particular aldehyde and indole determining the chromophoric material that is produced. The reaction of indoles with aldehydes, commonly termed the Ehrlich reaction, occurs under acidic conditions and is believed to involve an electrophilic attack by the pyrrole portion of the indole on the aldehyde carbonyl group.

Based upon the teachings of the prior art, it is very surprising that no acid catalyst is required to initiate the color forming reaction between the indoles and aldehydes on hair. Indeed, it is unexpected that hair should be such an efficient accelerator of this reaction.

Preferably the indole used in the present invention will have the structure

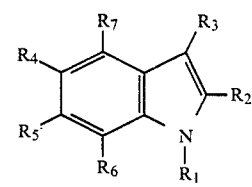

wherein $R_1$, $R_2$, $R_3$, $R_4$ and $R_5$ are each selected from H, $CH_3$, ethyl, propyl, isopropyl, alkoxy, aryl, and aryloxy; and wherein $R_2$, $R_4$-$R_7$ are each selected from H, OH, $NO_2$, $NH_2$, N(alkyl)$_2$, N(alkoxyl)$_2$, N(hydroxyalkoxy)$_2$, and aryl.

The aldehyde used will preferably have the structure

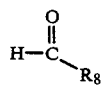

wherein $R_8$ is selected from H, $CH_3$, alkyl, alkenyl, alkynyl, benzyl, aminobenzyl, dialkylaminobenzyl, dialkoxylaminobenzyl, cinnamyl, aminocinnamyl, dialkylaminocinnamyl, dialkoxylaminocinnamyl, nitrobenzyl, alkylbenzyl, alkoxybenzyl, phenol, dihydroxyphenyl, trihydroxyphenyl, nitrohydroxyphenyl, hydroxycinnamyl, and acetamidophenyl.

Specific indole derivatives useful herein are exemplified by skatole, 5,6-dihydroxyindole,4-,5-,6-, or 7-hydroxyindole, 5-aminoindole, N-methylindole, 5-, or 6-, or 5,-6-benzyloxindole, methylene-5,6-dioxyindole and the like. Mixtures of the foregoing may also be employed.

The conditions under which the indole and aldehyde components are brought together, i.e. reacted, are generally well-known. It is generally preferred, however, that the contacting of these reagents take place at a pH of about 2 to about 10.

While the invention has been described above, the details of the present invention will be best understood by recourse to the following examples:

EXAMPLES
GENERAL COMMENTS

In the following examples the indole compound is added to an aqueous ethanol solution(10 to 40% ethanol). Preferably the indole is completely dissolved in the aqueous ethanol solution. Alternatively, the indole may be added to a gel based medium such as is obtained by mixing, on a weight percent basis, with the following formulation; deionized water (58%), Cellosize QP 4400 (1.1), ammonium lauryl sulfate (6.0), citric acid (1.6), SD alcohol 40 (33.0) and Polysorbate 20 (0.2). Additionally a thickened dye base may be made by mixing water (85%), carbopol-40 (1.5%), ethanol (12%) and monoethanolamine (1.5%) to which the indole and aldehyde may be added together or separately.

The indole mixture is then worked into the hair, followed by application of the aldehyde, which may also be in an aqueous ethanol solution of a gel base. Alternatively, the hair can be contacted with a combined mixture of the aldehyde and the indole for from about 5 to 30 minutes, shampooed and then dried. An intensely colored dye-out that proves to be long wearing and resistant to shampooing as well as to light exposure is obtained. Furthermore, the formed color is generally resistant to oxidation even under alkaline conditions.

EXAMPLE 1

Using the sequential application procedure outlined above, a sample of blended grey hair was dyed with 5-aminoindole and 4-N,N-dimethylaminocinnamaldehyde. After contacting the hair with 3% $H_2O_2$ at pH 9.5 for 15 minutes or exposing the swatch to artificial sunlight for 10 hours, the only change in the dye-out is a moderate loss of the red tones.

EXAMPLES 2-34

Using the same procedures as outlined in the general comments above and as used in Example 1, a number of samples of blended gray (BG) hair, and bleached (BL) hair were dyed in-vivo by the sequential reaction of an indole and an aldehyde separately. Total dye-out times of 15 minutes followed by shampooing were used. The amount of indole and aldehyde used was 1% of each on a wt/wt basis. Examples 2-34 are in Table 1 which shows the specific indole and aldehyde used and the results obtained.

TABLE 1

| Example | Indole* | Aldehyde* | Hair Type | Dyeout and comments |
|---|---|---|---|---|
| 2 | DAI | DACA | BG | Light yellow golden-brown. |
| 3 | " | " | BL | Yellow-orange. |
| 4 | NCH$_3$DH | 2,4OBZ | BG | Dark grey w/yellow tones. |
| 5 | " | " | BL | Mousy light brown. |
| 6 | NCH$_3$DHI | DACA | BG | Light brown w/yellow tones. |
| 7 | " | " | BG | pH 9 H$_2$O$_2$ bleachout of Ex. 6, = golden brown w/yellow. |
| 8 | " | " | BL | Dark yellow-brown. |
| 9 | " | " | BL | pH 9 H$_2$O$_2$ bleach out of Ex. 8 = mousy brown. |
| 10 | " | DMAB | BG | Violet w/brown tones. |
| 11 | " | DMAB + 2,4OBZ | BG | Dark violet w/yellow tones. |
| 12 | 5AI | DMAB | BG | Dark yellow orange. |
| 13 | " | " | BG | pH 9 H$_2$O$_2$ post-treatment of Ex. 12 = medium golden brown. |
| 14 | 5AI | 2,4OBZ | BG | Intense fluorescent yellow. |
| 15 | " | " | BG | pH 9 H$_2$O$_2$ post-treatment of Ex. 13 = darkening of Ex. 14. |
| 16 | " | " | Brown Hair | Gives yellow tones. |
| 17 | " | " | BG | 10 hrs. Fad-o-meter of Ex. 14 = slight darkening |
| 18 | " | DACA | BG | Intense brown w/red-violet. |
| 19 | " | " | BG | pH 9 H$_2$O$_2$ post-treatment of Ex. 18 = intense brown. |
| 20 | " | " | BG | 10 hrs. Fad-o-meter of Ex. 18 = lightens. |
| 21 | " | " | BL | Deep cherry red w/violet. |

TABLE 1-continued
EXAMPLES 2-34

| Example | Indole* | Aldehyde* | Hair Type | Dyeout and comments |
|---|---|---|---|---|
| 22 | " | " | BL | pH 9 $H_2O_2$ post-treatment of Ex. 21 = deep cherry red. |
| 23 | " | " | BL | 10 hrs. Fadometer of Ex. 21 = loses violet tones. |
| 24 | " | DACA + 2,4OBZ | BG | Medium brown w/red orange tones. |
| 25 | " | " | BG | 10 hrs. Fad-o-meter of Ex. 24 = loses some reds. (dark strawberry blonde). |
| 26 + | " | " | BL | Intense burnt orange w/red tones. |
| 27 | " | " | BL | 10 hrs. Fad-o-meter of Ex. 26 = loses some reds. |
| 28 | 5AI + NCH3DHI | 2,4OBZ | BG | Dark grey w/some yellow tones. |
| 29 | " | " | BG | pH 10 $Cu^{+2}$ post-treat of Ex. 28 = dark brown-yellow. |
| 30 | " | DMAB | BG | Dark golden brown w/orange tones. |
| 31 | " | " | BG | pH 10 $Cu^{+2}$ post-treat of Ex. 30 = Dark grey w/brown-gold tones. |
| 32 | 5AI | GL | BG | Medium ash brown. |
| 33 | In | DACA | BG | Golden brown w/red tones. |
| 34 | In | GL | BG | Dark grey-brown. |

*Abbreviations;
DAI = 5,6-diacetoxyindole;
DACA = 4-N,N-dimethylaminocinnmaldehyde;
MDI = 5,6-Methylenedioxyindole;
DMAB = 4-n,n-dimethylaminobenzaldehyde;
NCH3DHI = 5,6-dihydroxy-N-methylindole;
2,4OBZ = 2,4-dihydroxybenzaldehyde;
5AI = 5-aminoindole;
GL = glyceraldehyde;
In = indole.

EXAMPLES 35-48

A number of additional samples of blended grey (BG) hair and bleached (BL) hair were dyed by first mixing the aldehyde and indole together in an alcohol-water based dye medium such as obtained by dissolving the indole and the aldehyde in an alcohol such as ethanol (30% vol/vol), adding this to 68 ml of water along with Cabosil gel agent or xantham gum (2 gm) with rapid stirring to produce the gel dye medium.

This mixture is then applied to the hair sample for 15 minutes, followed by shampooing, to yield a long lasting dye-out. The amount of indole and aldehyde used was 1% of each on a wt/wt basis. These examples are set forth in Table 2 which provides a listing of the specific indole and aldehyde used for each example and the results obtained for each.

TABLE 2
EXAMPLES 35-48

| | Indole-aldehyde* | Hair Type | Color |
|---|---|---|---|
| 35 | DAI + DACA | BG | Medium gray-violet |
| 36 | " | BL | Violet |
| 37 | MDI + DMAB | BG | Light brown-violet |
| 38 | " | BL | Violet-brown |
| 39 | NCH3DHI + 2,4OBz | BG | Light brown-violet |
| 40 | " | BL | Light violet |
| 41 | NCH3DHI + DACA | BG | Intense medium golden brown. |
| 42 | " | BL | Intense medium orange brown. |
| 43 | 5AI + DACA | BL | Intense cherry red |
| 44 | 5AI + DMAB | BG | Medium golden orange-brown. |
| 45 | In + DACA | BG | Light auburn |
| 46 | 5AI + GL | BG | Medium brown |
| 47 | In + GL | BG | Light grey w/violet tones. |

TABLE 2-continued
EXAMPLES 35-48

| | Indole-aldehyde* | Hair Type | Color |
|---|---|---|---|
| 48 | In + Acct | BG | Pale blue-green |

*Abbreviations:
DACA = 4-N,N-dimethylaminocinnamaldehyde;
DAI = 5,6-diacetoxyindole;
NCH3DHI = 5,6-dihydroxy-N-methylindole;
MDI = methylenedioxyindole;
2,4OB$_z$ = 2,4-dihydroxybenzaldehyde;
DMAB = 4-N,N-dimethylaminobenzaldehyde;
5AI = 5-aminoindole;
In = indole;
GL - glyceraldehyde;
Acct = acetaldehyde.

While the invention has been described with respect to various specific examples and embodiments, it is to be understood that the invention is not limited thereto, reference being had to the appended claims for a definition of the scope of the invention.

I claim:

1. A hair dye composition comprising a combination of an indole of formula I:

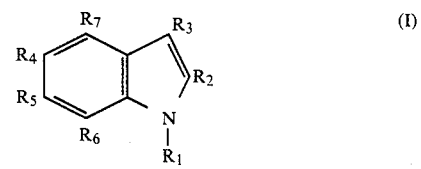

wherein $R_1$ and $R_2$ are each independently selected form H, $CH_3$, ethyl, propyl, isopropyl, alkoxy, aryl, and aryloxy; and wherein $R_2$ and $R_4$ through $R_7$ are each independently selected from H, $CH_3$, ethyl, propyl, isopropyl, OH, alkoxy, $NO_2$, $NH_2$, N(alkyl)$_2$, N(alkoxy)$_2$, N(hydroxy alkoxy)$_2$, halogen, aryl, aryloxy and acetoxy and an aldehyde of formula II:

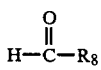
(II)

wherein $R_8$ is selected from $CH_3$, alkyl, alkenyl, alkynyl, benzyl, aminobenzyl, dialklaminobenzyl, dialkoxyaminobenzyl, cinnamyl, aminocinnamyl, dialkyaminocinnamyl, dialkoxyaminocinnamyl, nitrobenzyl, alkylbenzyl, alkoxybenzyl, phenol, dihydroxyphenyl, trihydroxyphenyl, nitrohydroxyphenyl, hydroxycinnamyl and acetamidophenyl in a reaction medium having a pH of about 2 to about 10.

2. A method for dyeing natural fibers, including human hair, comprising treating said natural fiber with a combination of an indole component and an aldehyde component and allowing said combination to react in the presence of the natural fiber, wherein the indole is of formula I:

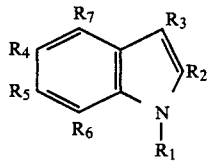
(I)

wherein $R_1$ and $R_3$ are each independently selected from H, $CH_3$, ethyl, propyl, isopropyl, alkoxy, aryl, and aryloxy; and wherein $R_2$ and $R_4$ through $R_7$ are each independently selected from H, $CH_3$, ethyl, propyl, isopropyl, OH, alkoxy, $NO_2$, $NH_2$, N(alkyl)$_2$, N(hydroxy alkoxy)$_2$, halogen, aryl, aryloxy and acetoxy and the aldehyde of formula II:

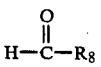
(II)

wherein $R_8$ is selected from $CH_3$, alkyl, alkenyl, alkynyl, benzyl, aminobenzyl, dialkylaminobenzyl, dialkoxyaminobenzyl, cinnamyl, aminocinnamyl, dialkylaminocinnamyl, dialkoxyaminocinnamyl, nitrobenzyl, alkylbenzyl, alkoxybenzyl, phenol, dihydroxyphenyl, trihydroxyphenyl, nitrohydroxyphenyl, hydroxycinnamyl and acetamidophenyl, said reaction taking place in the presence of a suitable medium.

3. A method according to claim 2 wherein said indole component is first applied to the natural fiber and then said aldehyde component is applied.

4. A method according to claim 2, wherein the aldehyde component is first applied to the natural fiber and then said indole component is applied.

5. A method according to claim 2, wherein the pH a medium used is between about 2 and about 6.5.

6. A method according to claim 2, wherein the indole component and the aldehyde component are premixed in an alcohol-water medium to form an indole-aldehyde adduct prior to treating said natural fiber to be dyed with said adduct.

7. A method according to claim 6, wherein the pH of the medium is between about 2 and about 10.

8. A method according to claim 6, wherein the medium used is an aqueous ethanol solution.

9. A method according to claim 6, wherein the medium used is a gel based medium.

10. A method according to claim 9, wherein the gel based medium has the following formulation:

| | |
|---|---|
| Cellosize QP4400 | 1.1 wt. % |
| ammonium laurylsulfate | 6.0 wt. % |
| citric acid | 1.6 wt. % |
| SD alcohol 40 | 33.0 wt. % |
| Polysorbate 20 | 0.2 wt. % |
| deionized water | q.s. 100 wt. % |

11. The composition of claim 1 wherein the indole reactant is selected form the group consisting of 5,6-diacetoxyindole, 5-amino indole, and N-methyl-5,6-dihydroxyindole.

12. The composition of claim 11 wherein the aldehyde reactant is selected from the group consisting of 4-N,N-dimethylamino-cinnamaldehyde, 4-N,N-dimethylamino benzaldehyde, and 2,4-dihydroxybenzaldehyde.

13. The composition of claim 1 wherein the indole and aldehyde reactants are 5-aminoindole and 4-N,N-dimethylamino cinnamaldehyde.

14. The method of claim 2 wherein the indole reactant is selected from the group consisting of 5,6-diacetoxyindole, 5-aminoindole, and N-methyl-5,6-dihydroxyindole.

15. The method of claim 14 wherein the indole reactant is selected from the group consisting of 4-N,N-dimethylamino cinnamaldehyde, 4-N,N-dimethylaminobenzaldehyde, and 2,4-dihydroxybenzaldehyde.

16. The method of claim 2 wherein the indole and aldehyde reactants are 5-aminoindole and 4-N,N-dimethylamino cinnamaldehyde.

* * * * *